United States Patent [19]
Johnson

[11] 3,965,750
[45] June 29, 1976

[54] LIQUID SAMPLER AND STERILIZER
[76] Inventor: Julius Theodore Johnson, 348 - 20th St., SE., Cedar Rapids, Iowa 52403
[22] Filed: Feb. 21, 1975
[21] Appl. No.: 551,699

[52] U.S. Cl. ................................................ 73/425.4 R
[51] Int. Cl.² ........................................... G01N 1/10
[58] Field of Search ............ 73/425.4 R, 425.4 P, 73/425.2; 215/321, 38; 220/306

[56] References Cited
UNITED STATES PATENTS

| | | | |
|---|---|---|---|
| 1,077,538 | 11/1913 | Magni | 215/321 |
| 3,313,159 | 4/1967 | Vanderbeck | 73/425.4 R |
| 3,318,155 | 5/1967 | Johnson | 73/425.4 R |
| 3,779,083 | 12/1973 | Ayres et al. | 73/425.4 P |

Primary Examiner—Richard E. Aegerter
Assistant Examiner—Willis Little
Attorney, Agent, or Firm—Johnston, Keil, Thompson & Shurtleff

[57] ABSTRACT

Sampling device adapted for sampling of liquids with strata of varying composition embodying an elongated tube with a well cap loosely mounted on one end thereof, an elastomer cap with an air vent hole mounted on the other end thereof, and a second elongated tube adapted to contain sterilizing liquid and in which the sampling device is placed when not in use.

7 Claims, 4 Drawing Figures

U.S. Patent    June 29, 1976    3,965,750
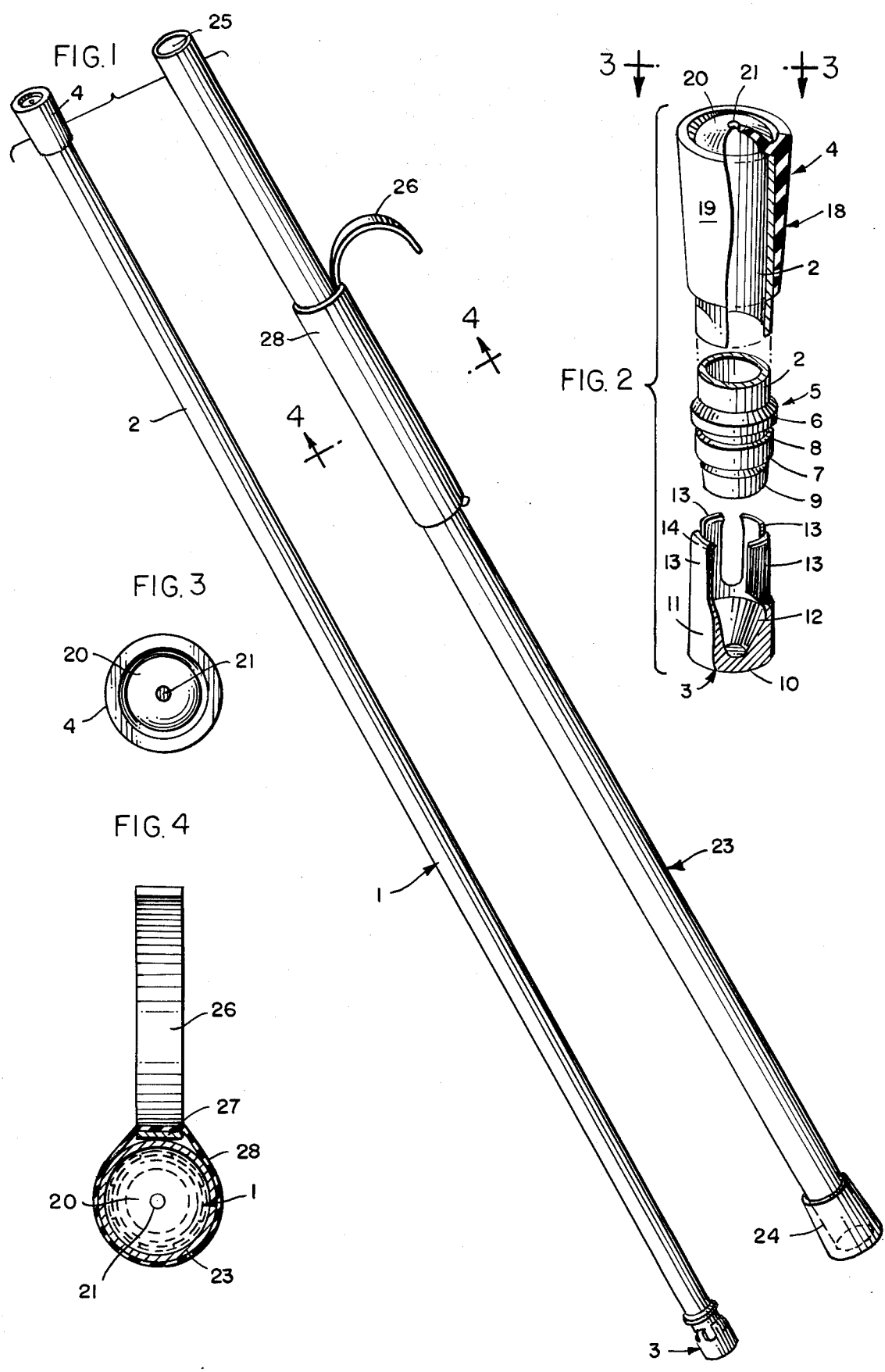

LIQUID SAMPLER AND STERILIZER

This invention relates to improvements in sampling devices for sampling of liquids with strata of varying composition of the general type shown in my U.S. Pat. No. 3,318,155. The invention particularly pertains to improvements in the technique of mounting the well cap at the lower end of the sampling tube so that it can rotate and pivot to a limited degree in order that the lower end of the sampling tube and the well cap can be thoroughly cleansed before taking samples of liquids with strata of varying composition.

The sampling tube herein disclosed is adapted for sampling of such liquid in tanks or vessels having a constant horizontal cross section, e.g., an upwardly cylindrical tank, a rectilinear tank and the like. The invention further embodies a combination of the sampling tube housed in a second tube adapted to hold a sterilizing liquid, particularly a combination utilizing an elastomer cap on one end of the sampling tube to close and seal the open end of the tube for housing the sampling tube.

Briefly, the sampling device of the subject invention embodies an elongated, open ended sampling tube having a well cap, later described, mounted on one end thereof and preferably also having an elastomer cap with at least one air vent hole mounted on the other end thereof.

The well cap is on the lower end of the sampling tube when the latter is used for sampling of liquids by lowering the sampling tube slowly through the full depth of the liquid being sampled. An end wall and side wall means form in the lower end of the well cap a liquid-retaining well. The lower end of the sampling tube projects into the upwardly facing side of the well a sufficient distance so that, when the sampling tube is completely withdrawn from the liquid being sampled, the lower end of the sampling tube is immersed in liquid retained in the well. This prevents air from entering the lower end of the sampling tube and loss of sample before it can be placed in the container for the sample.

When the sampling tube has been lowered slowly throughout the full depth of the liquid being sampled, the upper end of the tube is sealed against entry of air into the upper end of the tube, e.g., by placing a finger over an air vent hole. This is done as the sampling tube is raised from its full depth immersion and is continued until the sample in the sampling tube is ready to be put in its container. By so doing, all of the liquid which entered the sampling tube as it was slowly lowered through the full depth of the liquid being sampled will be retained in the sampling tube and will not flow out the lower end as the tube is being raised through the liquid and also lifted out of the liquid except for a small amount forced out by the pressure head of the liquid in the sampling tube.

The well cap is mounted on the lower end of the sampling tube by a plurality of upwardly extending fingers having inwardly bent, upper tips which are seated in an annular groove provided on the outside of the lower end of the sampling tube. The fit of the tips of the fingers in the annular groove is a loose fit, which allows the well cap to be rotated and/or tilted to a limited degree relative to the sampling tube. This loose fit is important for cleansing of the lower end of the sampling tube and the well cap, i.e., by rotating and/or tilting the well cap as the sampling tube is immersed in or flushed with cleansing liquid.

The sampling tube preferably is housed in a sanitizing tube of substantially equal length to the sampling tube. The sanitizing tube may contain a sterilizing liquid for immersing most or all of the sampling tube when it is placed in the sanitizing tube. An elastomer cap on the end of the sampling tube opposite the end bearing the well cap preferably serves the dual function of providing an air vent hole or holes for the sampling tube and for sealing the open end of the sanitizing tube when the former is placed in the latter.

A preferred form of the invention is illustrated in the drawings, wherein:

FIG. 1 is a perspective view of the sampling tube and the sanitizing tube in separated relationship;

FIG. 2 is a fragmentary, exploded view in perspective of the upper and lower ends of the sampling tube of FIG. 1;

FIG. 3 is a top plan view of the elastomer cap on the sampling tube as viewed from section 3—3 of FIG. 2; and FIG. 4 is a cross section of the sanitizing tube taken on section plane 4—4 of FIG. 1.

Referring to the drawings, the sampling tube 1 comprises an elongated, open ended tube 2 of constant internal cross section. A well cap 3 is mounted on one end of said tube and an elastomer cap 4 is mounted on the other end of said tube.

Orienting the sampling tube 1 in its normal liquid-sampling position, i.e., substantially vertical, and referring particularly to FIG. 2, the lower end 5 of the sampling tube 2 has an outwardly projecting annular upper shoulder or ring 6 and axially spaced therefrom a lower annular shoulder or ring 7. These shoulders or rings 6 and 7 provide therebetween an annular groove 8. The lowermost end 9 of the tube 2 projects into the liquid-holding portion of the well cap 3 when the latter is mounted on the lower end of the tube 2, as hereinafter described.

The well cap 3 comprises a closed end wall 10 and a side wall 11 forming an upwardly facing liquid-holding well 12. The well 12 may be cylindrical but preferably is of frusto-conical shape. The well cap 3 is mounted on the lower end of the tube 2 by a plurality of upwardly projecting, slightly springable fingers 13, four such fingers being used in the illustrated embodiment. The fingers 13 have slightly inwardly bent upper tips 14 dimensioned so that the inwardly bent tips will pass tightly over the lower annular shoulder or ring 7, e.g., with slight springing of the fingers 13. These fingers fit loosely in the annular groove 8 but cannot pass the upper annular shoulder or ring 6 after the fingers have been slid across the lower annular shoulder or ring 7. The well cap can be removed from the tube 2 by manually forcing its fingers 13 to slide across the shoulder or ring 7 by pulling the well cap away from the lower end of the tube 2.

When the well cap 3 is assembled on the lower end of the sampling tube 2 as aforedescribed, the lower edge of the lowermost end portion 9 is within the well 12, i.e., in a position where liquid flowing into the lowermost end 9 of the tube 2 must flow downwardly between the fingers 13 and into the well 12 and thence upwardly into the lower end of the sampling tube. This arrangement allows free flow of the liquid being sampled into the well and thence into the lower end of the tube 2 but prevents air from entering the lower end of the sampling tube 2 as the latter is taken substantially vertically out of the liquid being sampled. Thus, this arrangement provides a liquid trap serving as an air seal of the type described in several of the embodiments shown in my U.S. Pat. No. 3,318,155.

The opposite or upper end of the sampling tube 2 must be closed against entry of air when the filled sampled tube is begun to be withdrawn vertically from the liquid sample. For this purpose this end of the sampling tube 2 is provided with an elastomer cap 4 having a cylindrical inner wall seating tightly about the upper end of the sampling tube 2. Referring especially to FIG. 2, the elastomer cap 4 has a tapered, substantially frusto-conical outer surface 18 of its substantially cylindrical side wall 19. The cap 4 further comprises an elastomer end wall 20 having therein an air vent hole or passage 21. Air is prevented from entering the upper end of the sampling tube 2 by pressing the finger or thumb against the end wall 20 sufficiently tightly to seal off flow of air through the hole or passage 21.

When not in use, the sampling tube unit 1 is placed in the sanitizing tube 23, which has a slightly larger internal diameter than the largest diameter of any part of the sampling tube 2, in the illustrated case, the annular shoulder or ring 6. One end of the sanitizing tube 23 is completely closed by any suitable means, e.g., the mounting of an elastomer cap 24 thereon. The other end of the sanitizing tube 23 is an open end 25 having an inner diameter of a size to sealingly engage the tapered outer wall 18 of the elastomer cap 4. Thus, the cap 4 serves as a seal for the open end 25 and also as a means for releasably but securely holding the sampling tube unit 1 in the sanitizing tube 10. As aforestated, the sanitizing tube 23 may contain a sterilizing liquid or other liquid for maintaining the sampling tube unit 1 in a clean, sanitary condition when not in use. The cap 4 seals the open end 25 of the sanitizing tube against loss of any liquid contained in the sanitizing tube.

For convenience or support of the sanitizing tube while not in use, e.g., on a milk tank truck which collects milk from a number of firms and/or dairies, the sanitizing tube 23 is provied with a hook 26 having a shank 27. The hook 26 and shank 27 are adjustably mounted at any desired position along the sanitizing tube 23 by use of an elastomer tube or sleeve 28, which extends about the sanitizing tube 23 and the shank 27 of the hook 26 (FIGS. 1 and 4).

The invention accordingly provides improvements in sampling tubes of the aforedescribed type in which all portions of the samping tube, including the well cap and the parts of the sampling tube used to support the well cap both rotatably and tiltably can be readily cleansed between sampling uses. The invention further provides a sanitizing storage tube for the sampling tube to maintain the cleansed sampling tube in sanitary condition between uses of the sampling tube.

The best sampling technique with the subject sampling device is one of lowering the sampling tube in a substantially vertical orientation slowly through the full depth of the liquid being sampled. In order to take into the sampling tube proportionate volumes of strata of different compositions, the sampling tube should be lowered through the liquid at a rate slow enough that the liquid level in the tube remains substantially even with the upper liquid level of the liquid body. The upper end of the sampling tube remains vented to the air throughout the tube-lowering procedure.

When the well cap touches the bottom of the tank containing the liquid being sampled, the air vent passage at the upper end of the sampling tube is then closed or sealed and the sampling tube is withdrawn, again preferably substantially vertically, from the body of liquid. Its contents are then emptied into a sample container so that the liquid sample may be later analyzed to ascertain the contents of the liquid which is sampled, e.g., to ascertain the overall butterfat content and other qualities of milk.

If desired, when the well cap touches the bottom wall of the tank, the sampling tube may be tilted to take in additional liquid to compensate for the small amount of sampled liquid forced out by the pressure head of the liquid in the sampling tube. The additional liquid is then essentially the liquid which is lost due to the pressure head. This is explained in greater detail in column 5 of my U.S. Pat. No. 3,318,155.

It is thought that the invention and its numerous attendant advantages will be fully understood from the foregoing description, and it is obvious that numerous changes may be made in the form, construction and arrangement of the several parts without departing from the spirit or scope of the invention, or sacrificing any of its attendant advantages, the form herein disclosed being a preferred embodiment for the purpose of illustrating the invention.

The invention is hereby claimed as follows:

1. A sampling device useful for sampling liquids with strata of different compositions comprising an elongated tube having on one end thereof annular groove means, a well cap having bottom and side walls defining a liquid-holding well with an open side facing said tube, said end of said tube extending into said liquid-holding well, said cap further having peripherally spaced, axial fingers extending from its open side, the ends of said fingers being seated loosely in said groove means in a manner allowing rotation and limited tilting of said cap on said end of said tube, the liquid being sampled flowing between said fingers and into said end of said tube via said well cap as the tube is lowered substantially vertically through the body of liquid being sampled, and, with said tube held vertically, said end of said tube extending into said well providing, after said tube is filled with liquid to be sampled, a seal preventing air from entering the said end of said tube when said tube is raised completely out of said body of liquid.

2. A sampling device as claimed in claim 1, wherein the opposite end of said tube has means providing a small air venting passage allowing air to escape from said tube as it fills with liquid being sampled from a body of liquid and adapted to be closed as the sample-filled tube is raised upwardly through and out of said body of liquid.

3. A sampling device as claimed in claim 1, wherein the opposite end of said tube has mounted thereon an elastomer cap with a small air vent passage in said cap and adapted to be sealed by placing a finger or thumb over said passage.

4. A sampling device as claimed in claim 3, said device being housed in a second tube, one end of said second tube being closed and the other end of said tube being open, and said elastomer cap being seated tightly in said open end when the sampling device is fully inserted into said second tube.

5. A sampling device as claimed in claim 1, said device being housed in a second tube, one end of said second tube being closed and the other end being open, said device being inserted in said open end, a hook having a shank lying against said second tube, and an elastomer sleeve positioned about said second tube and said shank to thereby mount said hook on said second tube.

6. A sampling device as claimed in claim 1, wherein said annular groove means is an annular groove between two axially spaced, annular shoulders on said one end of said elongated tube.

7. A sampling device as claimed in claim 1, wherein said annular groove means is an annular groove between two axially spaced, annular shoulders on said one end of said elongated tube and said fingers having slightly inwardly bent tips dimensioned so that said tips will pass tightly over the annular shoulder contiguous to said one end, and the other annular shoulder being of a configuration which precludes said fingers from passing said last-mentioned annular shoulder.

* * * * *